(12) United States Patent
Rosenberg

(10) Patent No.: US 11,850,135 B2
(45) Date of Patent: Dec. 26, 2023

(54) PROSTHETIC IMPLANT DELIVERY DEVICE UTILIZING SURFACE ACTIVE AGENTS

(71) Applicant: Proximate Concepts LLC, Fort Lee, NJ (US)

(72) Inventor: Paul Rosenberg, Saddle River, NJ (US)

(73) Assignee: PAUL H. ROSENBERG FAMILY TRUST, Saddle River, NJ (US)

( * ) Notice: Subject to any disclaimer, the term of this patent is extended or adjusted under 35 U.S.C. 154(b) by 400 days.

(21) Appl. No.: 16/983,608

(22) Filed: Aug. 3, 2020

(65) Prior Publication Data
US 2021/0085444 A1    Mar. 25, 2021

Related U.S. Application Data

(60) Provisional application No. 62/881,487, filed on Aug. 1, 2019.

(51) Int. Cl.
*A61F 2/12*    (2006.01)
*A61F 2/00*    (2006.01)
(Continued)

(52) U.S. Cl.
CPC ............. *A61F 2/0095* (2013.01); *A61F 2/12* (2013.01); *A61L 31/10* (2013.01); *A61L 31/16* (2013.01);
(Continued)

(58) Field of Classification Search
CPC ........ A61F 2/0095; A61F 2/12; A61F 2/0059; A61L 31/16; A61L 33/0011; A61L 2400/10
See application file for complete search history.

(56) References Cited

U.S. PATENT DOCUMENTS

| 279,555 A | 6/1883 | Fish |
| 426,165 A | 4/1890 | Brittin |

(Continued)

FOREIGN PATENT DOCUMENTS

| CN | 201076483 Y | 6/2008 |
| FR | 2733903 A1 | 11/1996 |

(Continued)

OTHER PUBLICATIONS

Allergan. Delivery Assistance Sleeve, Directions for Use, Jul. 12, 2011. 7 pages.

(Continued)

*Primary Examiner* — Keri J Nelson
*Assistant Examiner* — Rebecca Lynee Zimmerman
(74) *Attorney, Agent, or Firm* — Leason Ellis LLP

(57) ABSTRACT

An apparatus for use in a surgical procedure for delivering a prosthetic implant comprises a flexible sleeve configured with a first end and a second end, the flexible sleeve being tapered such that a width of a region at the second end is relatively smaller than a width of a region at the first end, and an interior surface of the flexible sleeve that form an interior cavity, the interior cavity being sized to receive the prosthetic implant; one or more surface active coatings are applied to the interior cavity. The flexible sleeve is manipulatable such that when the prosthetic implant is positioned within the interior cavity, a manually applicable directional pressure in the direction of the second end causes the prosthetic implant to extrude from the second end.

8 Claims, 4 Drawing Sheets

(51) Int. Cl.
  *A61L 31/16* (2006.01)
  *A61L 31/10* (2006.01)
  *A61L 33/00* (2006.01)
  *A61F 2/08* (2006.01)

(52) U.S. Cl.
  CPC ... *A61L 33/0011* (2013.01); *A61F 2002/0894* (2013.01); *A61F 2210/0076* (2013.01); *A61L 2400/10* (2013.01)

(56) References Cited

U.S. PATENT DOCUMENTS

| | | |
|---|---|---|
| 568,411 A | 9/1896 | Pratt |
| 1,409,544 A | 3/1922 | Hallock |
| 1,486,078 A | 3/1924 | Dumont |
| 1,612,383 A | 12/1926 | Lepeshkin |
| 2,935,241 A | 5/1960 | Brady |
| 3,138,821 A | 6/1964 | Macciocchi et al. |
| 3,156,240 A | 11/1964 | Harrison et al. |
| 3,157,312 A | 11/1964 | Kitterman |
| 3,324,906 A | 6/1967 | Chu |
| 3,769,971 A | 11/1973 | Collins |
| 3,883,902 A | 3/1975 | Lynch |
| 4,035,850 A | 7/1977 | Cresswall |
| 4,143,428 A | 3/1979 | Cohen |
| 4,358,028 A | 11/1982 | Chiquiar-Arias |
| 4,641,648 A | 2/1987 | Shapiro |
| 4,650,833 A | 3/1987 | Sakagami et al. |
| 4,955,906 A | 9/1990 | Coggins et al. |
| 5,052,554 A | 10/1991 | Leonard |
| 5,067,821 A | 11/1991 | Young |
| 5,090,597 A | 2/1992 | Johnson |
| 5,150,706 A | 9/1992 | Cox et al. |
| 5,201,779 A | 4/1993 | Shiao |
| 5,222,630 A | 6/1993 | Burtis |
| 5,277,234 A | 1/1994 | Warstler |
| 5,366,116 A | 11/1994 | Burtis |
| 5,407,208 A | 4/1995 | Keller et al. |
| 5,500,019 A | 3/1996 | Johnson et al. |
| 5,571,178 A | 11/1996 | Ledergerber |
| 5,630,843 A | 5/1997 | Rosenberg |
| 5,723,006 A | 3/1998 | Ledergerber |
| 5,787,944 A | 8/1998 | Sarkis et al. |
| 6,019,776 A | 2/2000 | Preissman et al. |
| 6,033,411 A | 3/2000 | Preissman |
| 6,231,615 B1 | 5/2001 | Preissman |
| 6,238,799 B1 | 5/2001 | Opolski |
| 6,309,420 B1 | 10/2001 | Preissman |
| 6,348,055 B1 | 2/2002 | Preissman |
| 6,383,191 B1 | 5/2002 | Zdeblick et al. |
| 6,520,989 B1 | 2/2003 | Eaton |
| 6,743,523 B1 | 6/2004 | Woo et al. |
| 6,790,238 B1 | 9/2004 | Martin |
| 6,866,936 B2 | 3/2005 | Opolski |
| 7,048,743 B2 | 5/2006 | Miller et al. |
| 7,137,995 B2 | 11/2006 | Studin |
| 7,267,885 B1 | 9/2007 | Woo et al. |
| 7,510,579 B2 | 3/2009 | Preissman |
| 7,645,301 B2 | 1/2010 | Hudgins et al. |
| 7,775,716 B2 | 8/2010 | Ejeblad |
| 8,206,443 B2 | 6/2012 | Preismann |
| 8,555,893 B2 | 10/2013 | Keller et al. |
| 8,641,758 B1 | 2/2014 | Anderson et al. |
| 9,023,114 B2 | 5/2015 | Buevich et al. |
| 9,168,126 B2 | 10/2015 | Presimann |
| 9,402,713 B2 | 8/2016 | Keller et al. |
| 9,925,028 B1 | 3/2018 | Rosenberg |
| 10,058,415 B2 | 8/2018 | Preissman |
| 2001/0012968 A1 | 8/2001 | Preissman |
| 2005/0267543 A1 | 12/2005 | Heruth et al. |
| 2006/0184100 A1 | 8/2006 | Studin |
| 2007/0038310 A1 | 2/2007 | Guetty |
| 2007/0191964 A1 | 8/2007 | Preissman |
| 2007/0276484 A1 | 11/2007 | Abell et al. |
| 2008/0241212 A1 | 10/2008 | Moses et al. |
| 2009/0024228 A1* | 1/2009 | Lesh ............... A61F 2/12 623/23.72 |
| 2009/0099588 A1 | 4/2009 | Makower et al. |
| 2009/0204107 A1 | 8/2009 | Keller et al. |
| 2010/0168808 A1 | 7/2010 | Citron |
| 2010/0028061 A1 | 11/2010 | Preisman |
| 2011/0035003 A1 | 2/2011 | Preismann |
| 2011/0082546 A1 | 4/2011 | Freund |
| 2012/0143331 A1 | 6/2012 | Keller et al. |
| 2012/0143332 A1 | 6/2012 | Keller et al. |
| 2013/0073040 A1 | 3/2013 | Preissman |
| 2014/0074235 A1 | 3/2014 | Keller et al. |
| 2014/0074236 A1 | 3/2014 | Keller et al. |
| 2015/0028056 A1 | 1/2015 | Massis |
| 2015/0032208 A1 | 1/2015 | Preissman |
| 2015/0126812 A1 | 5/2015 | Anderson |
| 2015/0238262 A1 | 8/2015 | Buevich et al. |
| 2015/0272731 A1 | 10/2015 | Racchini et al. |
| 2016/0008171 A1 | 1/2016 | de Juan, Jr. et al. |
| 2016/0095697 A1 | 4/2016 | Anderson |
| 2016/0199174 A1 | 7/2016 | Keller et al. |
| 2016/0302914 A1 | 10/2016 | Keller et al. |
| 2016/0310304 A1 | 10/2016 | Mialhe |
| 2018/0116779 A1 | 5/2018 | Marx |
| 2019/0107250 A1 | 4/2019 | Rosenberg |
| 2019/0117365 A1* | 4/2019 | Winn ............ A61B 17/3468 |
| 2020/0008923 A1* | 1/2020 | Geiger ............ A61F 2/0095 |

FOREIGN PATENT DOCUMENTS

| | | |
|---|---|---|
| WO | 2010126462 A1 | 11/2010 |
| WO | 2012177587 A1 | 12/2012 |

OTHER PUBLICATIONS

Bell et al. "An illuminating no-touch device for breast augmentation," Can J Plast Surg, Mar. 2009, vol. 17, No. 1, pp. 30-31.
Supplementary European Search Report for European Patent Application No. 09844125.6 completed on Aug. 30, 2012. 2 pages.
No Author. Claim Chart regarding Ledergerber U.S. Pat. No. 5,723,006 Feb. 28, 2012. 7 pages.
Pearne et al. Letter from Pearne & Gordon regarding Ledergerber U.S. Pat. No. 5,723,006 Feb. 28, 2012. 1 page.
Mladick. "No Touch" Submascular Saline Breast Augmentation Technique, Aesth. Plast. Surg. 17:183-192, 1993.
Mladick. No-Touch Sleeve, Finesse in Breast Augmentation, 2000 Byron Medical. 1 page.
Examination Report in corresponding Colombian Patent Application No. NC2017/0011485 dated Feb. 23, 2018. 2 pages.
Extended European Search Report for European Patent Application No. 17197722.6 dated Apr. 11, 2018. 9 pages.
Galdiero et al. "Microbial Evaluation in Capsular Contracture of Breast Implants." Plastic and reconstructive surgery, Jan. 2018, 141.1: 23-30.
No Author. "AvertPlus Surface Active Antimicrobial Coating." BioInteractions. 2016. http://www.biointeractions.com/pdfs/avertplus_overview.pdf. Retreived on Aug. 3, 2018. 1 page.
No Author. "Astute Advanced Heparin Coating." BioInteractions. 2016. http://www.biointeractions.com/pdfs/astute_overview.pdf. Retreived on Aug. 3, 2018. 1 page.
Examination Report in corresponding Colombian Patent Application No. NC2018/0012376 dated Aug. 21, 2020.

\* cited by examiner

PROSTHETIC IMPLANT DELIVERY DEVICE UTILIZING SURFACE ACTIVE AGENTS

CROSS REFERENCE TO RELATED APPLICATION

The present application claims the benefit of U.S. application Ser. No. 62/881,487, filed Aug. 1, 2019, which is hereby incorporated by reference in its entirety.

INCORPORATION BY REFERENCE

The following disclosures are hereby incorporated herein by reference, each in its entirety:
U.S. Pat. No. 10,058,415, filed on Oct. 21, 2015, entitled "SILICONE BREAST IMPLANT DELIVERY," and assigned at issue to Keller Medical, Inc.;
U.S. Pat. No. 6,743,523, filed on Mar. 16, 2000, entitled "MULTIPLE LAYER FILM OF A NEW NON-PVC MATERIAL", and assigned at issue to Baxter International, Inc.; and
U.S. Pat. No. 7,267,885, filed on Mar. 16, 2000, entitled "CONTAINERS AND PEELABLE SEAL CONTAINERS OF NEW NON-PVC MATERIAL," and assigned at issue to Baxter International, Inc.

FIELD OF INVENTION

This invention is directed to a delivery apparatus for facilitating the insertion of a silicone implant, such as a breast prosthesis, into a surgically developed pocket.

BACKGROUND OF THE INVENTION

This invention relates to the placement of silicone implants within a patient's body. Silicone implants have been in worldwide use for a number of years. While marketing of the implants was halted within the United States for over 15 years, the use of silicone implants has resumed within the United States. One problem with silicone implants is that the implants are provided in a filled condition and must be inserted into a surgical pocket. As a result, traditional surgical approaches require the use of larger incisions in comparison to saline implants which can be inserted through small incisions which are later filled in situ with saline.

While many patients prefer the more natural qualities of silicone, patients remain apprehensive because of the larger incisions and possibility for visible scars which result from silicone implants.

An additional concern with the use of silicone implants is that the conventional insertion process can compromise the longevity and integrity of the implants. A typical insertion process involves hand manipulation by the surgeon of the implant in order to insert it into the surgical pocket. Studies have shown that implant failures are often associated with an area of minor damage to the outer surface of the implant. The damaged areas are believed to correlate to excessive pressure applied by hand manipulation of the implant and/or damage associated with a "nick" of the implant surface by a "touching" injury such as a fingernail or insertion that damages the implant.

An additional consideration with respect to silicone implants involves the amount of time required to insert the implants. A traditional hand manipulation of an implant into a surgical pocket can take between 10 to 20 minutes per implant for even a highly skilled surgical practitioner. Typically, hand manipulation of an implant requires the use of a larger incision and would be done with a saline implant. The amount of time required has a direct bearing on the expense of the procedure, the surgical expense reflecting the surgeon's time, the support staff within the operating room, and the amount of time allocated for the surgical procedure. Accordingly, any improvements to reduce the time required for implantation of the silicone implant will have significant cost savings with respect to the surgical procedure.

In addition to the foregoing, when any type of implant is inserted into a surgical pocket that a surgeon opens in the body of a patient, the body reacts by forming a protective lining around the prosthetic. This biological structure is referred to as the "capsule", "tissue capsule" or "scar capsule", though it should be noted that the structure it is not exactly the same as scar tissue. Although, a capsule formation is normal and happens regardless of whether the implant is smooth or textured, silicone or saline, some theorizes that problematic capsule growth is potentially attributed to manipulation of tissue during implant placement. In addition, trauma to tissue along or adjacent to the surgical pocket may suffer from the direct formation of scar tissue due to potentially over aggressive manipulation of tissue at the entry site for the implant along the edge of the surgical pocket.

Accordingly, there remains room for improvement and variation within the art.

SUMMARY OF THE INVENTION

It is one aspect of at least one of the present embodiments to provide an apparatus and a process for facilitating the delivery of a silicone implant into a surgically developed pocket.

It is a further aspect of at least one embodiment of the present invention to provide for an apparatus and process for facilitating the placement of a filled silicone implant into a surgical pocket through a surgical incision that is too small for a manual insertion of an implant.

It is a further aspect of at least one of the present embodiments to provide for an apparatus and process that allows insertion of a silicone implant through a sleeve defining a small diameter outlet into a patient without direct hand manipulation of the implant.

It is a further aspect of at least one of the present embodiments to provide for an apparatus and process that allows insertion of a silicone implant by passing the implant across the one or more surface active coatings as it exits the sleeve to cause interaction between the implant and the one or more surface active coatings. Such interaction allows the surface active coatings to provide one or more benefits that such coatings offer, such as exposure of the implant to the antimicrobial effects of a given surface active coating.

It is yet a further and more particular aspect of at least one aspect of at least one of the present embodiments to provide for a process and apparatus that allows for a "touchless" insertion of a silicone implant into a surgical pocket.

In accordance with one embodiment of the invention, an apparatus for use in a surgical procedure for delivering a prosthetic implant comprises a flexible sleeve configured with a first end and a second end, the flexible sleeve being tapered such that a width of a region at the second end is relatively smaller than a width of a region at the first end, and an interior surface of the flexible sleeve that form an interior cavity, the interior cavity being sized to receive the prosthetic implant; one or more surface active coatings are applied to the interior cavity. The flexible sleeve is manipulatable such that when the prosthetic implant is positioned within the interior cavity, a manually applicable directional pressure in the direction of the second end causes the prosthetic implant to extrude from the second end.

In addition to surface active coatings, embodiments of the present invention comprise the application of one or more lubricious coatings to the interior cavity of the flexible sleeve. The one or more lubricious coatings may be simultaneously applied to the interior cavity of the flexible sleeve in conjunction with a given one of the one or more surface active coatings. Focusing on the lubricious coating specifically, the lubricious coating may be water activated and, as such, comprises any hydrophilic gel that decreases a coefficient of friction on the interior surface. Turning to the one or more surface active coatings, exemplary surface active coatings include, but are not limited to, an antimicrobial coating and a heparin coating. The one or more surface active coatings may be applied serially, in a particular order, or simultaneously applied to the interior cavity.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DETAILED DESCRIPTION OF THE INVENTION

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus, or process pathway. To avoid redundancy, detailed descriptions of much of the apparatus once described in relation to a figure is not repeated in the descriptions of subsequent figures, although such apparatus or process is labeled with the same reference numbers.

Figure 1:
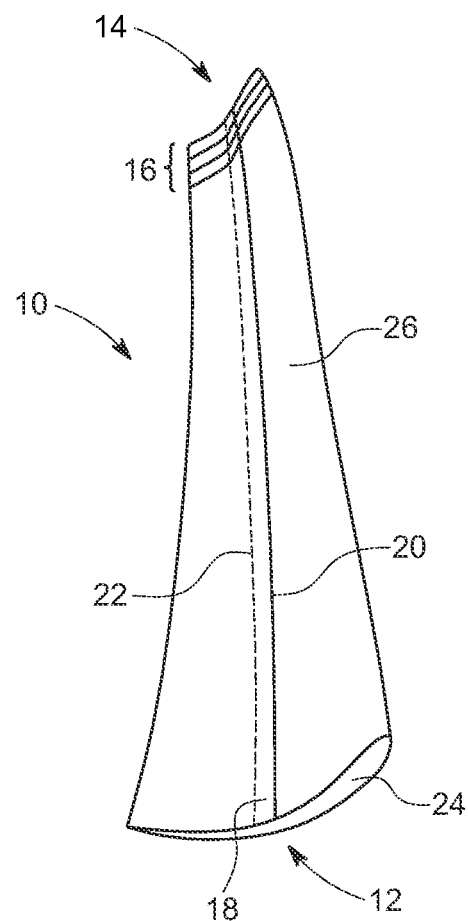
FIG. 1 is a perspective view of a prosthetic insertion sleeve along with a silicone prosthesis.
Figure 1:
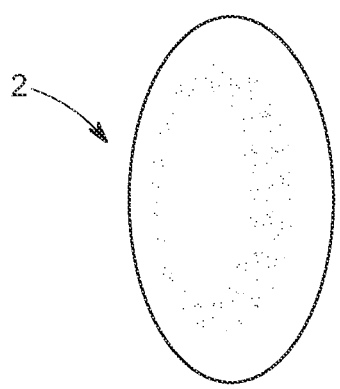
Figure 2:
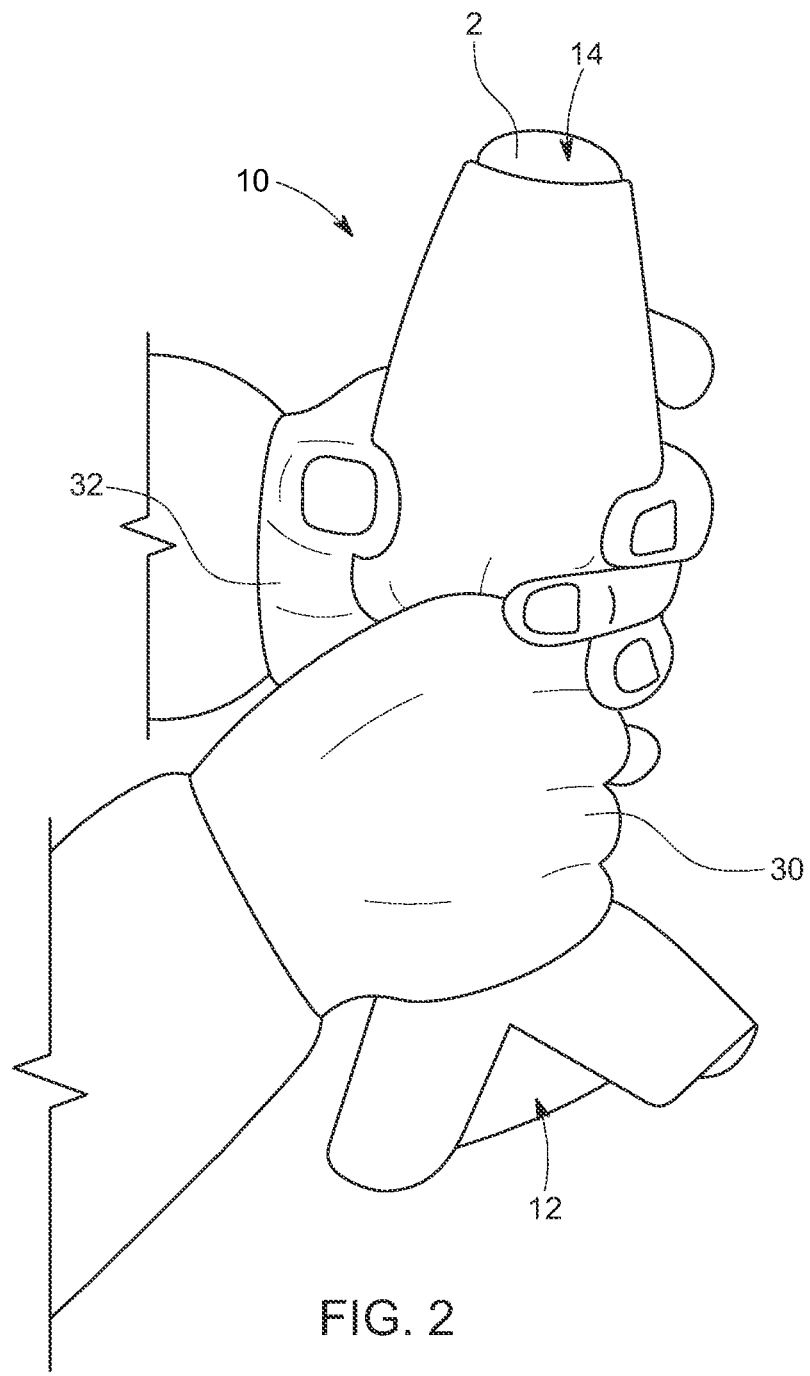
FIG. 2 is a picture of the insertion sleeve with the silicone implant positioned within the sleeve and showing further hand manipulation of the implant via the sleeve.
Figure 3:
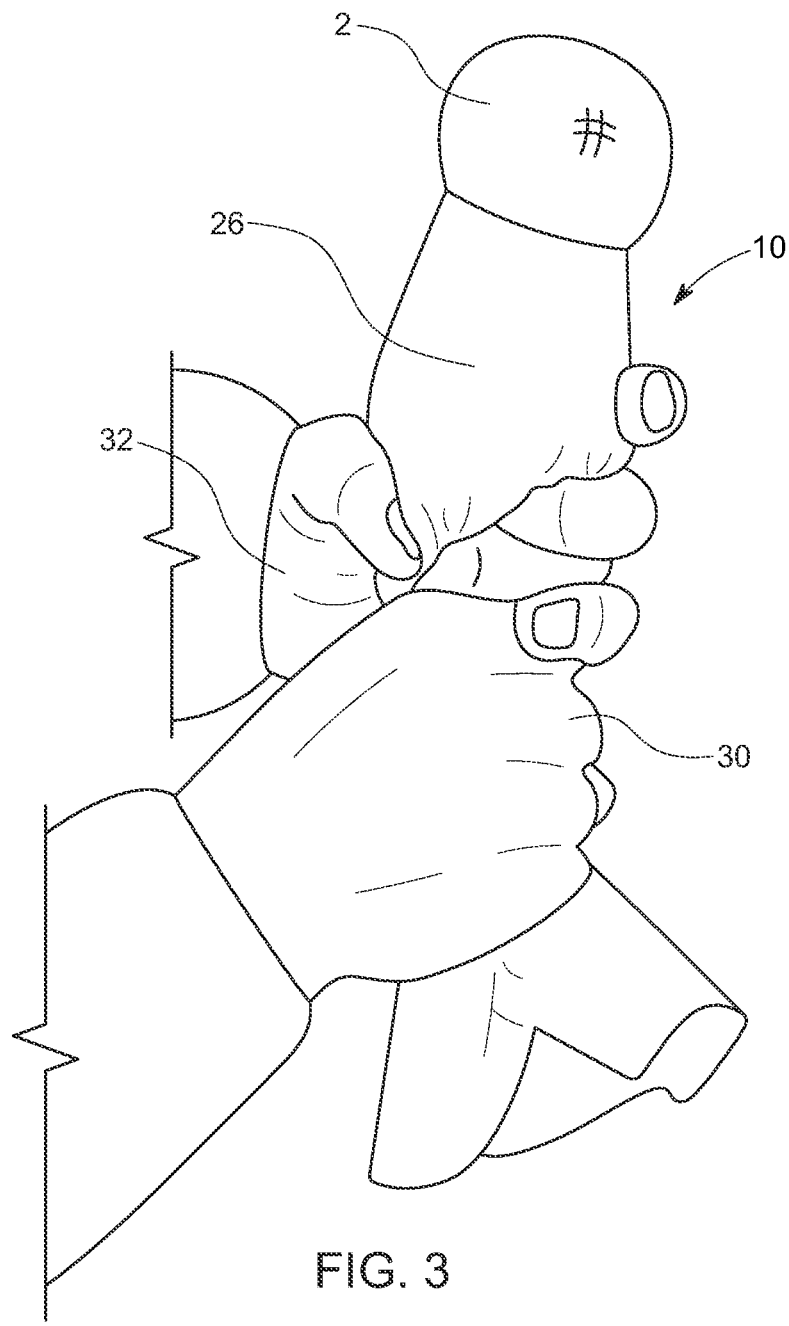
FIG. 3 is a view similar to FIG. 2 showing additional manipulation of the prosthesis through the sleeve and illustrating a portion of the prosthesis exiting a tapered end of the sleeve.

As seen in reference to FIGS. 1 through 3, a sleeve 10 is provided having a general conical shape and which defines a first opening 12 at a larger end of the sleeve and a smaller opening 14 along the tapered terminal tip of sleeve 10. As best seen in reference to FIG. 1, sleeve 10 may be provided by a material which is sufficiently flexible, and which enables the sleeve 10 to assume a flattened configuration for storage and shipping.

As seen in reference to FIGS. 2 and 3, when an implant 20, such as a silicone implant, is placed through opening 12 into the interior of sleeve 10, sleeve 10 can be manipulated to conform to the shape of the implant 20 as well as to apply pressure to direct the implant 20 along the length of the sleeve and toward opening 14.

Preferably, sleeve 10 is of a flexible material. In one embodiment of the invention, sleeve 10 can be provided by a fabric material such as a plastic-containing fabric which is pliable yet resistant to stretching. It is also envisioned that use of a transparent plastic or other suitable polymer material which has sufficient properties including flexibility and non-elasticity may be used. It is believed that there are advantages to using a transparent or semitransparent material to assist the surgeon in proper orientation of the implant 20 within the interior of sleeve 10. Suitable transparent materials may include Mylar®, plastics made from TYGON® brand of plastics, vinyl, polyvinyl chloride, and other similar materials. One suitable material which is flexible and transparent includes compositions of ethylene and alpha-olefin copolymers such as the compositions used in IV saline bags. Suitable multilayer films and sealed structures are taught in U.S. Pat. Nos. 6,743,523 and 7,267,885 both assigned to Baxter International Inc., and which are incorporated herein by reference. As disclosed therein, suitable films heat sealed to form suitable containers, are transparent with minimal hazing, and can be sterilized using gas sterilization or heat with intact seals and remain sufficiently flexible and pliable for the necessary manipulation described herein.

Other attributes of sleeve 10 include the ability to provide sleeve 10 as a sterile component. Accordingly, the material must be capable of withstanding at least one of several conventional sterilization techniques such as a steam autoclave, chemical gas sterilization, or irradiation. Additionally, the interior surface of sleeve 10 may preferably have a low coefficient of friction to facilitate passage of the implant 20 through the sleeve 10. It has been found that using a surgically appropriate lubricant will facilitate passage of the implant 20 through the interior of sleeve 10. Such lubricants may be applied directly to the implant 20 or the sleeve can be coated with lubricant or supplied pre-coated with a lubricant that is already present within sleeve 10.

Since the size of silicone implants 20 may vary in a range from about 150 cc to about 800 cc, the dimensions of opening 14 may be varied to accommodate various size implants 20. Preferably, sleeve 10 is provided with an opening 14 sized to fit the smallest implant. The tip opening 14 may be enlarged by cutting portions of the sleeve to provide a larger opening. If desired, indicia may be present on the exterior of sleeve 10 to allow the cutting of the sleeve to the proper dimensions for the size of the implant 20.

Alternatively, the tip opening 14 can have a diameter sized to allow the largest standard implant of 800 cc to exit the sleeve. According to this invention, it has been found that an opening 14 having a diameter of about 6 cm will allow delivery of the implant into the surgical pocket. As described below, use of an optional tip would allow for a sleeve to be provided having a single opening size to accommodate the largest implant. Selection of an appropriate tip can then be made based upon the size of the implant.

While it is believed preferable that sleeve 10 be provided from a single structural substrate, it is also recognized that an equivalent device can be provided of a flexible sleeve 10 having a separate inner liner (not illustrated) which may be present within the interior of sleeve 10. The liner could either be integral with sleeve 10 or may be a separate layer of material manually inserted within the interior of sleeve 10 at the time of use.

The larger opening 12 of sleeve 10 allows the implant to be placed within the sleeve with little force or manual manipulation. When the implant is within the interior of sleeve 10, the larger opening may be twisted closed as seen in FIGS. 2 and 3. Thereafter, the surgeon is able to apply manual pressure via the sleeve to the implant 20. The surgeon is thus able to apply pressure to the implant, forcing the implant toward the smaller opening 14. As seen in reference to FIGS. 2 and 3, the implant can be forced through the small opening 14.

As the surgeon is manipulating the implant through sleeve 10, the opening 14 is placed within the surgical pocket designed for receiving the implant. Accordingly, tip 14 is inserted through an incision associated with the surgical pocket. As the implant is forced through opening 14, the surgical pocket can be manipulated slightly to create a vacuum that assists in the placement of the implant into the pocket. Additionally, another useful feature of the apparatus and process is that as approximately half of the implant 20 has been exerted through opening 14, the remainder of the implant will flow through the sleeve without additional manipulation. Accordingly, once the opening 14 is positioned within the surgical pocket, implant 20 can be manipulated so that the prosthesis 20 is forced into the surgical pocket. The surgeon is able to control the positioning and orientation of the implant 20 by proper rotation and positioning of the sleeve 10 containing the implant 20.

It has been found that use of a sleeve 10 can greatly reduce the amount of time required for insertion of an implant 20. It has been found that the step of inserting a simple implant can occur within a timeframe of about 3 to 20 seconds minutes as compared to a time interval of 5 to 15 minutes for a traditional hand manipulation of an implant. Additionally, because the implant can be inserted through a small opening, the size of the surgical incision can be made smaller than would otherwise be required for a silicone implant.

The use of the sleeve 10 and implant 20 can be used with incisions. For instance, periareolar, trans axillary, intramammary incisions can be used with the above process and apparatus for insertion of an implant.

In accordance with this invention, it has been found beneficial to initially lubricate the exterior of implant 20 with an appropriate surgical lubricant such as K-Y® brand sterile lubricant. Following lubrication, the lubricated implant 20 is placed within the sleeve 10 and the implant 20 is forced through opening 14 as a pre-lubrication step. Following this pre-lubrication step, the implant can again be placed within the sleeve and subsequently inserted into the patient's surgical pocket.

It is also envisioned that, depending upon the coefficient of friction of the interior of sleeve 10 and/or any associated liner, it may be possible to provide other types of lubricants, including dry or powdered lubricant products to the interior of sleeve 10. Such lubricants are activated by being moistened and would provide an alternative to manually coating the prosthesis with a lubricant.

In addition to the application of a lubricant to interior surface of the sleeve 100, a number of disparate surface active coatings may also be applied to the interior surface of the sleeve 100. The use of surface active coatings on the interior surface of the sleeve 100 has advantages over drug eluting covers or coatings that may be applied to the surface of a medical device. One advantage of such surface active coatings over drug eluting coatings is that the surface active coatings do not elute or otherwise release from the interior surface of the sleeve, but rather remain bonded to the interior surface. A further distinction over the use of drug eluting compounds is that the mechanism of action for such surface active coatings is not a specific antibiotic that is targeted towards a specific genus and species of bacteria, but rather a broad based antimicrobial action based on cell membrane rupture of a given virus, bacteria, protozoa, microbe, etc.

According to one embodiment, a given one of the one or more surface active coatings is applied by dipping the sleeve, where the surface active coating is in a liquid phase, in a volume of the given surface active coating. Accordingly, the surface active coating may be simultaneously applied to one or more surfaces of the sleeve. Similarly, where the surface active coating is in liquid form, the surface active coating may be applied to a surface of the sleeve by spraying or airbrushing the surface active coating onto the desired surface. Likewise, vapor depositing and other coating techniques know to those of skill in the art may be used to apply the surface active coating to one or more surfaces of the sleeve. It should also be noted that multiple surface active coatings can be combined in solution for simultaneous application to the desired surfaces.

The surface active coating is cured, if required, which may be by heat, UV, etc., depending on the curing requirements of the specific surface active coatings. According to one embodiment, components of a first surface active coating are bonded to components of another surface active coating, which is itself then bonded to the surface of the sleeve, both of which may comprise bonding by way of a curing process. Curing allows for bonding of the one or more surface active coatings to bind to the sleeve, which may be ionic or covalent bonds, or combinations thereof, again depending on the specific surface active coatings applied to the surface of the sleeve, as well as any interactions therebetween.

As the implant moves through the interior of the sleeve towards the egress point at the distal end, the surfaces of the implant come into communication with the surface active coatings, which then interact with any foreign agents on the exterior surface of the implant prior to placement in the surgical pocket. Such communication between the prosthetic implant and the one or more surface active coatings allows the one or more coatings to impart one or more benefits that such coatings offer. For example, where the surface active coating has an antimicrobial component, the surface of the prosthetic implant receives the antimicrobial benefits of the surface active coating without any medication or drugs unnecessarily or undesirably eluting into the body of the patient.

The application of such surface active coatings is an advantageous improvement in the functioning of the surgical device in placing a prosthetic implant due to its ability to reduce the occurrence of infection and other complications that arise during and after placement. The issue involves the adhesion of bacteria onto an implantable medical device, such as a prosthetic implant. Adsorption of protein on the outer surface of the implantable device provides a suitable location for bacterial adhesion. Bacterial adhesion on the exterior surface of the prosthetic implant, even in minor amounts, has the possibility of leading to bacterial division, secretion and, ultimately, the development of biofilm across the surface of the prosthetic implant subsequent to its placement inside the patient. Again, the application of surface active coatings to the interior of the sleeve allows the surfaces of the prosthetic implant come into communication with the surface active coatings. This communication allows for the one or more surface active coatings to interact with any foreign agents on the exterior surface of the prosthetic implant prior to placement in the surgical pocket.

Figure 4:
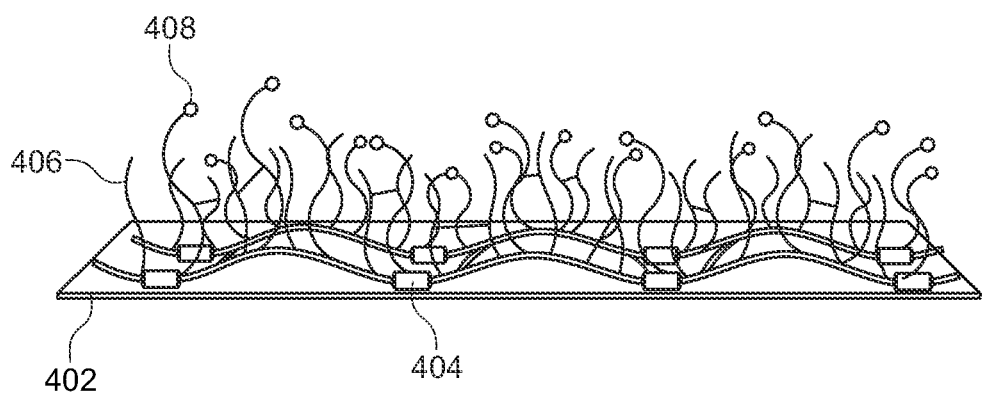
FIG. 4 is a picture of one or more surface active coatings that are bonded to an interior surface of the sleeve.

FIG. 4 illustrates one exemplary surface active coating for application to the interior surface of the sleeve. In the exemplary illustration of FIG. 4, the interior surface of the sleeve 402 has affixed thereto a coating that comprises a non-thrombogenic component 406 and an antimicrobial component 408. Each of the non-thrombogenic components 906 and antimicrobial components 408 are bonded to a polymer backbone 404 that is further bonded to the interior surface of the sleeve 402. One exemplary surface active coating that can be bonded to the interior surface of the sleeve to provide such non-thrombogenic and antimicrobial effects is the AdvertPlus™ surface active antimicrobial coating available from BioInteractions Ltd.

If desired, sleeve 10 can further define a structural tip (not illustrated) in association with opening 14. The tip could be provided of a more elastic material that facilitates insertion of the tip into the surgical pocket. For instance, a separate tip could provide for an extension beyond the existing opening 14 and which would have a narrower initial diameter providing a longer tip which may be more easily inserted within the interior of a surgical pocket. The ability of an optional tip to expand allows the implant 20 to pass through sleeve 10 and opening 14 while positioning the exiting implant 20 further within the surgical pocket. The use of the tip is believed beneficial in that it prevents the passage of the implant from extruding the sleeve from the incision. In other words, the tip provides a deeper positioning for the sleeve 10 more accurately directs the placement of the implant within the surgical pocket. The use of an expandable tip may facilitate the insertion time and lessen the learning curve for surgeons who are using the sleeve 10.

An important attribute of sleeve 10, including any optional tip structure 14, is that the interior surface of sleeve 10, including opening 14 and any associated tip member, must provide for a smooth and substantially uninterrupted passageway. It is important that any seams that may be formed or abutments between one type of material to another or from opening 14 to an associated tip must be of a sufficient smoothness such that the surface of the implant 20 is not degraded. Accordingly, it is envisioned that sonically welded seams or the use of a unitary extrusion process is desired for forming appropriate sleeves 10. In addition, to the extent opening 14 may be "cut to size", it is important that the material, once cut, not present any cutting artifacts or roughened edges that could damage the implant 20. Similarly, the identical concerns must be met by any optional tip used with sleeve 10 such that the material of the tip as well as its method of attaching the tip to the sleeve 10 and sleeve opening 14 must not present any potential implant contact surfaces that could result in damage to the implant.

Although embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

What is claimed is:

1. An apparatus for use in a surgical procedure for delivering a prosthetic implant, the apparatus comprising:
    a flexible sleeve configured with a first end and a second end, the flexible sleeve being tapered such that a width of a region at the second end is relatively smaller than a width of a region at the first end;
    an interior surface of the flexible sleeve that form an interior cavity, the interior cavity being sized to receive the prosthetic implant;
    a lubricious coating; and
    a surface active coating applied to the interior cavity, wherein the flexible sleeve is manipulatable such that when the prosthetic implant is positioned within the interior cavity a manually applicable directional pressure in the direction of the second end causes the prosthetic implant to extrude from the second end, wherein the surface active coating includes an antimicrobial coating component, and wherein the surface active coating comprises a heparin coating component.

2. The apparatus of claim 1, wherein the lubricious coating is water activated.

3. The apparatus of claim 2 wherein the lubricious coating comprises a hydrophilic gel that decreases a coefficient of friction on the interior surface.

4. The apparatus of claim 1 wherein the surface active coating comprises a homogenous mixture including the antimicrobial coating component and a non-thrombogenic coating component.

5. The apparatus of claim 1 wherein the prosthetic implant is selected from the set of prosthetic implants consisting of a breast implant, a pectoral implant, a calf implant, and a gluteal implant.

6. The apparatus of claim 1 wherein the flexible sleeve is fabricated from a material selected from the set of materials consisting of medical grade vinyl, medical grade PVC, medical grade nylon, and polyethylene.

7. The apparatus of claim 1, wherein the lubricious coating and the surface active coating are combined in solution and thereby define a homogenous mixture.

8. An apparatus for use in a surgical procedure for delivering a prosthetic implant, the apparatus comprising:
    a flexible sleeve configured with a first end and a second end, the flexible sleeve being tapered such that a width of a region at the second end is relatively smaller than a width of a region at the first end;
    an interior surface of the flexible sleeve that form an interior cavity, the interior cavity being sized to receive the prosthetic implant;
    a lubricious coating; and
    a surface active coating applied to the interior cavity, wherein the flexible sleeve is manipulatable such that when the prosthetic implant is positioned within the interior cavity a manually applicable directional pressure in the direction of the second end causes the prosthetic implant to extrude from the second end,
wherein the surface active coating includes an antimicrobial coating component, and wherein the surface active coating comprises a homogenous mixture including the antimicrobial coating component and a non-thrombogenic coating component, and wherein the antimicrobial coating component and the non-thrombogenic coating component are bonded to a polymer backbone which is bonded to the interior surface.

* * * * *